(12) United States Patent
Groszmann et al.

(10) Patent No.: US 9,351,800 B2
(45) Date of Patent: May 31, 2016

(54) HYBRID TRACKING SYSTEM UTILIZING COMBINED LED AND MAGNETORESISTANCE SENSORS

(75) Inventors: Daniel Eduardo Groszmann, Cambridge, MA (US); William Hullinger Huber, Scotia, NY (US); Jon Thomas Lea, Salt Lake City, UT (US); Laurent Jacques Node-Langlois, Salt Lakt City, UT (US); Christopher Allen Nafis, Rexford, NY (US)

(73) Assignee: General Electric Company, Schenectady, NY (US)

( * ) Notice: Subject to any disclaimer, the term of this patent is extended or adjusted under 35 U.S.C. 154(b) by 1556 days.

(21) Appl. No.: 12/979,095

(22) Filed: Dec. 27, 2010

(65) Prior Publication Data

US 2012/0165657 A1    Jun. 28, 2012

(51) Int. Cl.
*G01R 33/09* (2006.01)
*A61B 19/00* (2006.01)
*H01L 27/15* (2006.01)
*H01L 33/48* (2010.01)

(52) U.S. Cl.
CPC .............. *A61B 19/54* (2013.01); *G01R 33/093* (2013.01); *A61B 2019/5251* (2013.01); *A61B 2019/5255* (2013.01); *A61B 2019/5483* (2013.01); *A61B 2019/5495* (2013.01); *A61B 2562/06* (2013.01); *H01L 27/15* (2013.01); *H01L 33/48* (2013.01)

(58) Field of Classification Search
CPC ................... A61B 19/5244; A61B 2019/5251; G01R 33/093
USPC ............................................. 324/207.21, 252
See application file for complete search history.

(56) References Cited

U.S. PATENT DOCUMENTS

| 7,440,479 | B2 * | 10/2008 | Nurmikko ....................... 372/37 |
| 8,283,921 | B2 * | 10/2012 | Huber et al. ................... 324/252 |
| 8,358,128 | B2 * | 1/2013 | Jensen et al. .................. 324/252 |
| 8,483,800 | B2 * | 7/2013 | Jensen et al. .................. 600/424 |

* cited by examiner

*Primary Examiner* — Reena Aurora

(57) ABSTRACT

A hybrid tracking system utilizing at least one combined light emitting diode (LED) and magnetoresistance sensor. The hybrid tracking system includes optical tracking technology and electromagnetic (EM) tracking technology with at least one combined LED and magnetoresistance reference sensor attached to a fixed object, at least one combined LED and magnetoresistance sensor attached to an object being tracked, and a processor coupled to the at least one combined LED and magnetoresistance reference sensor and the at least one combined LED and magnetoresistance sensor for processing signals from the at least one combined LED and magnetoresistance reference sensor and the at least one combined LED and magnetoresistance sensor. The combined LED and magnetoresistance sensor includes at least one magnetoresistance sensor and at least one LED that are integrated into a single package.

19 Claims, 6 Drawing Sheets

HYBRID TRACKING SYSTEM UTILIZING COMBINED LED AND MAGNETORESISTANCE SENSORS

BACKGROUND OF THE INVENTION

This disclosure relates generally to hybrid tracking systems, and more particularly to a hybrid optical and electromagnetic (EM) tracking system utilizing combined light emitting diode (LED) and magnetoresistance sensors.

Medical practitioners, such as interventional radiologists, surgeons, and other medical professionals, often rely upon tracking or navigation systems when performing a medical procedure. Such systems may provide positioning and orientation information for a medical instrument or implant with respect to the patient or a reference coordinate system, for example. A medical practitioner may refer to the tracking system to ascertain the position and orientation of the medical instrument when the instrument is not within the practitioner's line of sight with regard to the patient's anatomy, or with respect to non-visual information relative to the patient. A tracking system may also aid in pre-surgical planning.

A tracking system allows the medical practitioner to visualize the patient's anatomy and track the position and orientation of the instrument. The medical practitioner may use the tracking system to determine when the instrument or implant is positioned in a desired location or oriented in a particular direction. The medical practitioner may locate and operate on, or provide therapy to, a desired or injured area while avoiding other structures. Increased precision in locating medical instruments within a patient may provide for a less invasive medical procedure by facilitating improved control over smaller, flexible instruments having less impact on the patient. Improved control and precision with smaller, more refined instruments may also reduce risks associated with more invasive procedures such as open surgery.

Tracking systems may be optical, ultrasonic, inertial, EM, or sonic, for example. Generally, each system includes its own advantages and disadvantages. For example, optical tracking is typically considered the most accurate tracking technology. However, optical tracking requires a line of sight. During the course of a surgical procedure, a line of sight path may become impossible to achieve. If the surgeon relies on optical tracking alone, navigation of the instrument or implant may be temporarily unavailable.

At such a point during a medical procedure, the surgeon may wish to employ another tracking technology, such as an EM tracking system. EM tracking systems allow for a surgeon to track a position and/or orientation of one sensor relative to another, without requiring a line of sight. However, due to electromagnetic interference caused by, among other things, metal objects in the operating environment, EM tracking systems may not always be the most accurate of the available tracking systems. Thus, at another point during the procedure, the surgeon may wish to again switch from the EM tracking system to another system.

While some current systems may allow for a surgeon to employ more than one tracking technology during a medical procedure, such systems typically do not allow for a dynamic change of tracking technologies. Further, this is achieved by providing various tracking systems along with a switch that will allow the clinician to select the appropriate tracking technology. Each tracking technology may be located at different location and the solution suggests combining existing the tracking systems to allow a surgeon to switch from one tracking technology to another in real time.

As mentioned earlier, at some point during a procedure, one or more unused tracking technologies may be more accurate than the currently used technology. At that point, the surgeon may wish to use a different tracking technology. If the surgeon is switching from one tracking system to another to use a different tracking technology, the issue of signal interference and calibration become significant. The calibration needs to be done based on the location of each tracking system and this might affect the quality of hybrid tracking systems. Thus instead of switching among different tracking systems, it will be beneficial to provided a tracking sensor unit incorporating different tracking technologies.

Therefore, a need exists for a hybrid tracking system for use in navigation of instruments and/or implants during medical, surgical and interventional procedures. Such a hybrid tracking system may provide multiple tracking technologies simultaneously during a medical, surgical and interventional procedure to assist in the accuracy of navigation instruments and/or implants during the procedure.

BRIEF DESCRIPTION OF THE INVENTION

In accordance with an aspect of the disclosure, a combined LED and magnetoresistance sensor comprising at least one magnetoresistance sensor and at least one light emitting diode (LED) that are integrated into a single package.

In accordance with an aspect of the disclosure, a hybrid tracking system comprising at least one combined LED and magnetoresistance reference sensor attached to a fixed object, at least one combined LED and magnetoresistance sensor associated with an object being tracked, and a processor coupled to the at least one combined LED and magnetoresistance reference sensor and the at least one combined LED and magnetoresistance sensor, wherein the processor is capable of processing signals from the at least one combined LED and magnetoresistance reference sensor and the at least one combined LED and magnetoresistance sensor.

In accordance with an aspect of the disclosure, a hybrid tracking system utilizing at least one combined LED and magnetoresistance sensor, the hybrid tracking system comprising at least one combined LED and magnetoresistance reference sensor attached to a fixed object, at least one combined LED and magnetoresistance sensor attached to an object being tracked, an optical tracking technology including a camera system to sense light emitted by a LED, an EM tracking technology including an EM transmitter for generating a magnetic field, and a processor coupled to the at least one combined LED and magnetoresistance reference sensor and the at least one combined LED and magnetoresistance sensor, wherein the processor is capable of processing signals from the at least one combined LED and magnetoresistance reference sensor and the at least one combined LED and magnetoresistance sensor.

Various other features, aspects, and advantages will be made apparent to those skilled in the art from the accompanying drawings and detailed description thereof.

DETAILED DESCRIPTION OF THE INVENTION

Figure 1A:
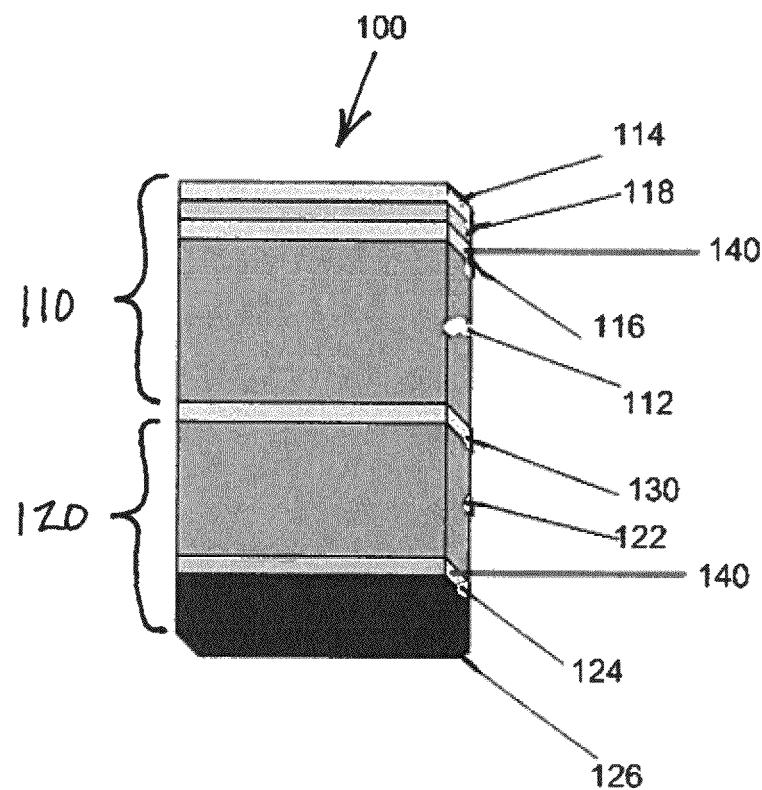
FIG. 1A is an enlarged view of an exemplary embodiment of a combined light emitting diode (LED) and magnetoresistance sensor semiconductor integrated circuit.
Figure 1B:
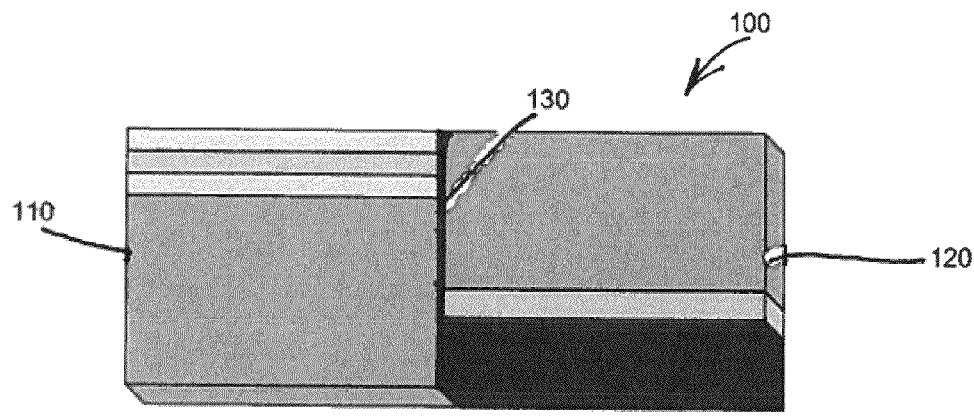
FIG. 1B is an enlarged view of an exemplary embodiment of a combined LED and magnetoresistance sensor semiconductor integrated circuit.
Figure 1C:
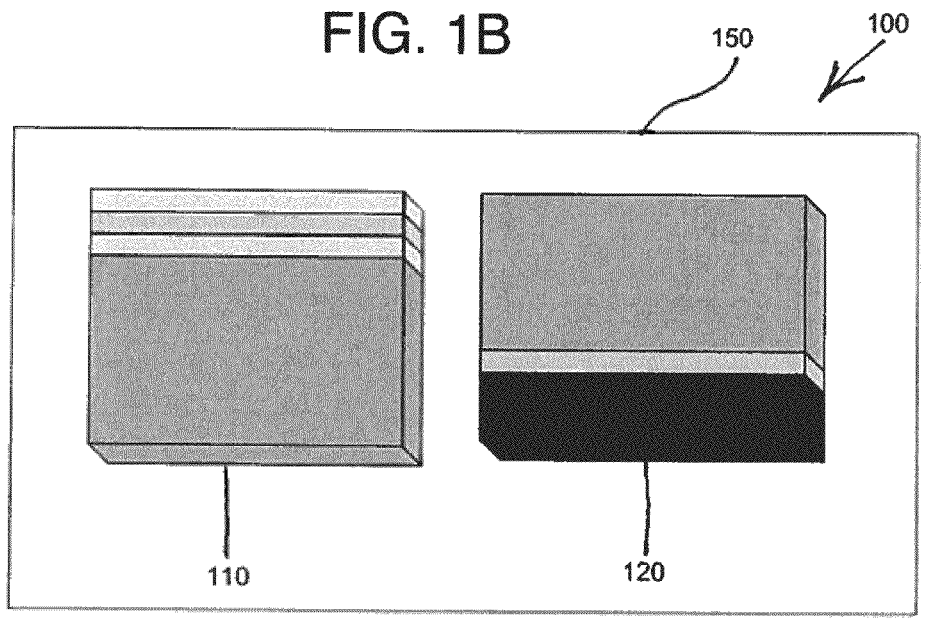
FIG. 1C is an enlarged view of an exemplary embodiment of a combined LED and magnetoresistance sensor semiconductor integrated circuit.

Referring now to the drawings. FIGS. 1A, 1B and 1C illustrate enlarged views of different exemplary embodiments of a combined light emitting diode (LED) and magnetoresistance sensor semiconductor integrated circuit 100. The combined light emitting diode (LED) and magnetoresistance sensor semiconductor integrated circuit 100 includes an LED 110 and a magnetoresistance sensor 120. The LED 110 and magnetoresistance sensor 120 may be integrated or manufactured as a single semiconductor integrated circuit to form a single LED and magnetoresistance sensor device.

In an exemplary embodiment, the LED 110 comprises a substrate 112, a p-doped region 114, an n-doped region 116 and an activation layer 118 deposited between the p-doped region 114 and the n-doped region 116. In an exemplary embodiment, the p-doped region 114 is adjacent to the substrate 112 or the n-doped region 116 is adjacent to the substrate 112.

In an exemplary embodiment, the magnetoresistance sensor 120 comprises an insulating substrate 122, an alternate pattern of a metal material and a semiconductor material deposited on a surface of the insulating substrate 122, represented as a magnetoresistance layer 124, and a bias magnetic material 126 deposited over the magnetoresistance layer 124.

In an exemplary embodiment, cathode and anode lead wires 140 extend from the combined LED and magnetoresistance sensor semiconductor integrated circuit 100 to supply a voltage across the semiconductor integrated circuit. At least one lead wire 140 may be coupled to the activation layer 118 and at least one lead wire may be coupled to the magnetoresistance layer 124.

The LED 110 emits lights based on line of sight path of an instrument, implant or other object that may be detected and tracked by a camera-based optical portion of the hybrid tracking system. The magnetoresistance sensor 120 provides a signal in response to an applied magnetic field. The magnetoresistance sensor 120 provides a change in electrical resistance of a conductor or semiconductor when a magnetic field is applied. The sensor's resistance depends upon the magnetic field applied. The bias magnet material 126 subjects the semiconductor material to a magnetic field required to achieve required sensitivity. The magnetoresistance sensor 120 provides a signal in response to the strength and direction of the applied magnetic field.

The magnetoresistance sensor 120 provides a very small form factor, excellent signal-to-noise ratio (low noise operation), and excellent low frequency response. Low noise combined with wide dynamic range enables the magnetoresistance sensor 120 to be used for position and orientation tracking in electromagnetic (EM) or hybrid tracking systems including EM tracking. The low frequency response of the magnetoresistance sensor 120 allows a position and orientation tracking system to operate at very low frequencies where metal tolerance is maximized.

In an exemplary embodiment, the magnetoresistance sensor 120 may be built with various architectures and geometries, including, giant magnetoresistance (GMR) sensors, anisotropic magnetoresistance (AMR) sensors and extraordinary magnetoresistance (EMR) sensors.

In an exemplary embodiment, the LED 110 and the magnetoresistance sensor 120 may be fabricated as separate semiconductor integrated circuits and coupled together with an epoxy material 130 to form a single combined LED and magnetoresistance sensor semiconductor integrated circuit 100, as shown in FIGS. 1A and 1B. Alternately, the LED 110 and magnetoresistance sensor 120 may be fabricated into a single semiconductor integrated circuit. In the embodiment shown in FIG. 1A, the substrate 112 of the LED 110 and the substrate 122 of the magnetoresistance sensor 120 are joined together with an epoxy material 130 to form the combined LED and magnetoresistance sensor semiconductor integrated circuit 100. In the embodiment shown in FIG. 1B, the LED 110 and the magnetoresistance sensor 120 are joined side by side using an epoxy material 130. The non-active layers or the substrates of LED 110 and the magnetoresistance sensor 120 may be joined together to form the combined LED and magnetoresistance sensor semiconductor integrated circuit 100. In the embodiment shown in FIG. 1C, the LED 110 and the magnetoresistance sensor 120 are not joined together, but are enclosed in an encapsulating lens 150.

The embodiments shown in FIGS. 1A, 1B and 1C are exemplary only, as the combined LED 110 and magnetoresistance sensor 120 may be integrated in various different forms and styles.

Many new clinical applications include the tracking and navigation of a variety of objects, instruments, implants and other medical devices, such as catheters, guidewires, and other endovascular instruments that require tracking sensors to be very small in size. The form factor of the combined LED and magnetoresistance sensor semiconductor integrated circuit 100 may be scaled to sizes less than 0.1 mm×0.1 mm.

Figure 2:
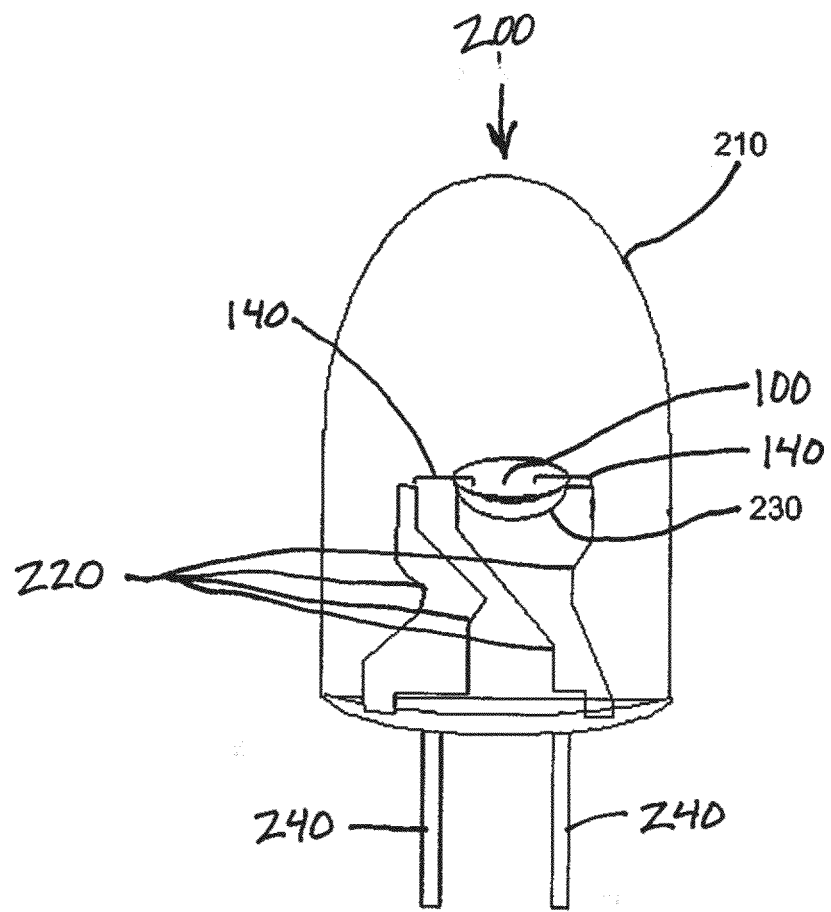
FIG. 2 is an enlarged view of an exemplary embodiment of a combined LED and magnetoresistance sensor integrated into a single device.

FIG. 2 illustrates an enlarged view of an exemplary embodiment of a combined LED and magnetoresistance sensor integrated into a single device 200. The combined LED and magnetoresistance sensor 200 co-locates an LED with a magnetoresistance sensor in a single package. The combined LED and magnetoresistance sensor 200 is encapsulated within an encapsulating lens 210. The combined LED and magnetoresistance sensor semiconductor integrated circuit 100 as described with reference to FIG. 1 is mounted within a reflector cup 230. The cathode and anode lead wires 140 extending from the combined LED and magnetoresistance sensor semiconductor integrated circuit 100 are coupled to multiple lead wires 220 that extend to leads 240 extending from the device 200. These leads 240 may be used to input and output signals from the combined LED and magnetoresistance sensor 200.

The embodiment shown in FIG. 2 is one example of a combined LED and magnetoresistance sensor 200 that could be packed in various different ways to form a combined LED and magnetoresistance sensor 200.

Figure 3:
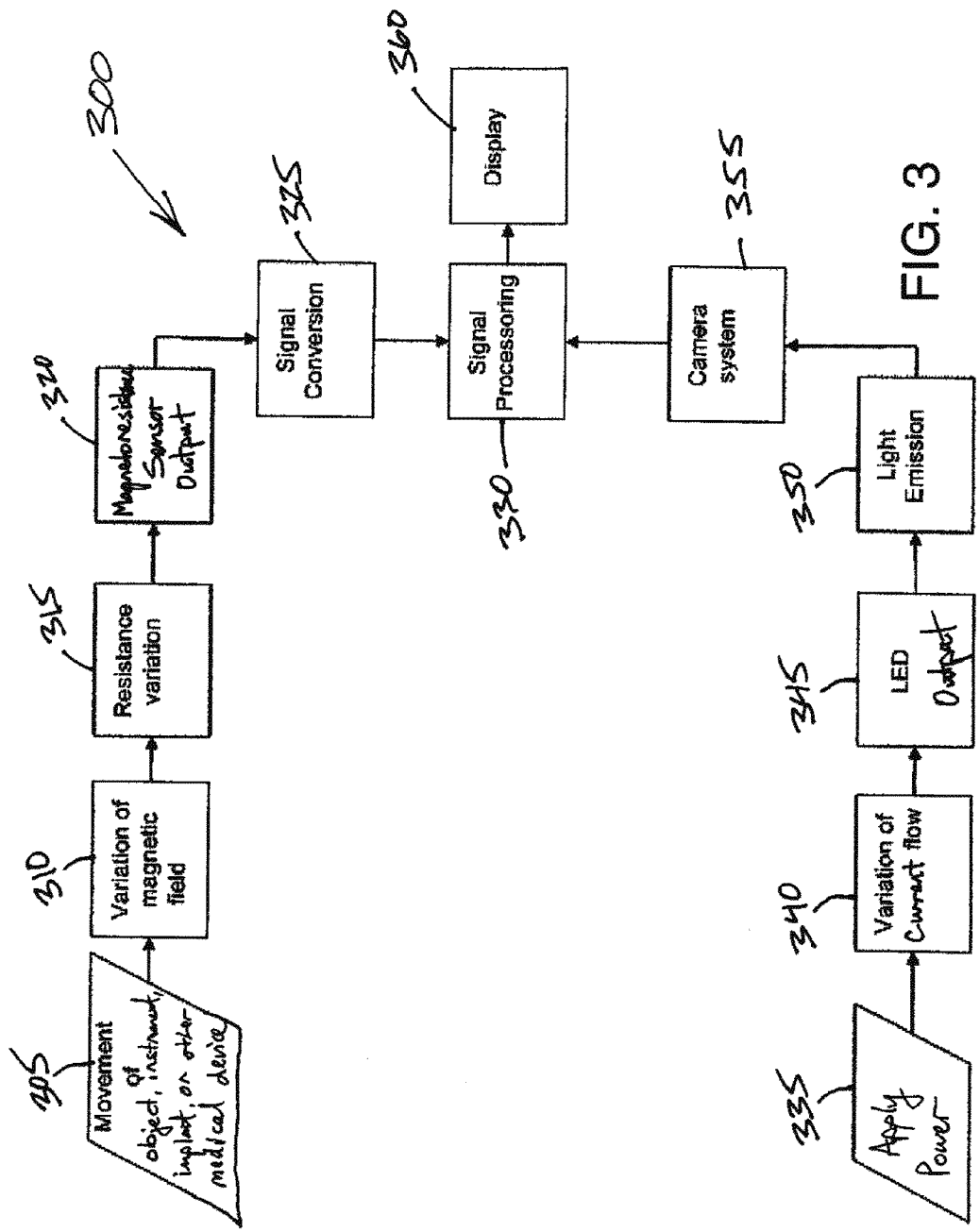
FIG. 3 is a flow diagram of an exemplary embodiment of the functional operation of a combined LED and magnetoresistance sensor used within a hybrid tracking system.

FIG. 3 illustrates a flow diagram 300 of an exemplary embodiment of the functional operation of a combined LED and magnetoresistance sensor 200 used within a hybrid tracking system. During medical, surgical or interventional procedures, the combined LED and magnetoresistance sensor 200 may be used as a reference sensor or a tracking sensor in a hybrid tracking system. The combined LED and magnetoresistance sensor 200 may be attached to an object to be tracked, an instrument or implant to be tracked, and/or a fixed reference to act as a fixed reference sensor. The combined LED and magnetoresistance sensor 200 incorporates an LED 110 and magnetoresistance sensor 120, as described with reference to FIG. 1. Both the LED 110 and magnetoresistance sensor 120 are active simultaneously and a processing device may be used to select the relevant signal for processing.

An optical tracking system typically includes either active LEDs that are visible to a camera system (usually infra-red) or with passive spherical reflectors that reflect light generated by a light source (usually infra-red) and detected by the camera system. There are usually at least three (3) fixed optical sensors (LEDs or spherical reflectors) that can be seen by at least two (2) cameras (stereo computer vision) to determine the position of the optical sensors in space. By knowing the fixed mechanical position of the optical sensors and comparing the measured locations of the optical sensors, the position and orientation of an object attached to the optical sensors may be determined and tracked.

An EM tracking system typically includes a plurality of EM sensors used to track the position and orientation of an object, an instrument, an implant or other medical device in relation to multidimensional images of a patient's anatomy. At least one of the plurality of EM sensors may be attached to an object to be tracked, an instrument to be tracked, an implant to be tracked, and/or a fixed reference to act as a fixed reference sensor. Additionally, the tracking system uses visualization tools to provide the interventional radiologist, surgeon or other medical practitioner with co-registered views of the object, instrument, implant or other medical device with the patient's anatomy.

The hybrid tracking system of the present disclosure incorporates both optical and EM tracking technology including a dual tracking component (a combined LED and magnetoresistance sensor) that allows the use of optical tracking for large distances or highly distorted EM environments and at the same time allows the use of EM tracking for removing line of sight issues and for tracking flexible instruments inside a patient's anatomy or other structures. No transformation from one tracking system to the other is necessary and no calibration of such a transformation is necessary.

The magnetoresistance sensors along with the EM tracking system work by tracking magnetic field variations to determine position and orientation of objects, instruments, implants or other medical devices, and the LEDs along with the optical (camera) tracking system works by tracking the location of the light source emitted by the LEDs to determine position and orientation of objects, instruments, implants or other medical devices.

The magnetoresistance sensor 120 provides an output corresponding to changes in electrical resistance of a conductor or semiconductor when a magnetic field is applied. The sensor's resistance depends upon the magnetic field applied. The bias magnet material 126 shown in FIG. 1 subjects magnetoresistance layer 124 to a magnetic field required to achieve required sensitivity. The magnetoresistance sensor 120 provides a signal in response to the strength and direction of a magnetic field. The application of a magnetic field confines the electrons to the magnetoresistance layer 124, resulting in an increased path length. Increasing the path length, increases the sensitivity of the magnetoresistance sensor 120.

Returning to the flow diagram 300 of the functional operation of a combined LED and magnetoresistance sensor 200 used within a hybrid tracking system. In an exemplary embodiment, the combined LED and magnetoresistance sensor 200 may be attached to an object, instrument, implant or other medical device to be tracked. When tracking the object, instrument, implant or other medical device using the EM portion of the hybrid tracking system, the object, instrument, implant or other medical device movement 305 will influence the bias magnet material in the magnetoresistance sensor and the bias magnetic material will provide a varying magnetic field on the magnetoresistance layer in the magnetoresistance sensor of the combined LED and magnetoresistance sensor at step 310. At step 315, this varying magnetic field will cause variations in resistance of the magnetoresistance layer. This change in resistance will be detected and provided as an output of the magnetoresistance sensor at step 320. The output of the magnetoresistance sensor is converted to an appropriate form at step 325 before proceeding to the signal processing step 330. When tracking the object, instrument, implant or other medical device using the optical portion of the hybrid tracking system, power (a voltage) is applied to the LED at step 335, and based on the power applied, the biasing of the p-doped region and the n-doped region changes and results in current flow through the activation layer at step 340. At step 345, the changes in current flow through the activation layer causes the LED to emit light as an output. The light emitted by the LED at step 350 makes a line of sight path from the object, instrument, implant or other medical device being tracked to the camera detectors of the camera system at step 355. The LED output signal corresponds to changes in the location of the emitted light caused by the movement of the object, instrument, implant or other medical device being tracked. The camera system output is provided for signal processing at step 330 and the tracking output is displayed on a display of the hybrid tracking system at step 360.

In an exemplary embodiment, the object, instrument, implant or other medical device being tracked may be tracked using at least one of the optical or EM technologies available with the combined LED and magnetoresistance sensor. In an exemplary embodiment, the object, instrument, implant or other medical device being tracked may be tracked using both the optical and EM technologies available, with both optical and EM output signals available simultaneously. An appropriate output signal may be selected while processing the signal and the processed signal may be displayed on a display of the hybrid tracking system. In addition, the reference sensor in the hybrid tracking system may be a combined LED and magnetoresistance sensor, which will provide reference information during a medical, surgical or interventional procedure.

Figure 4:
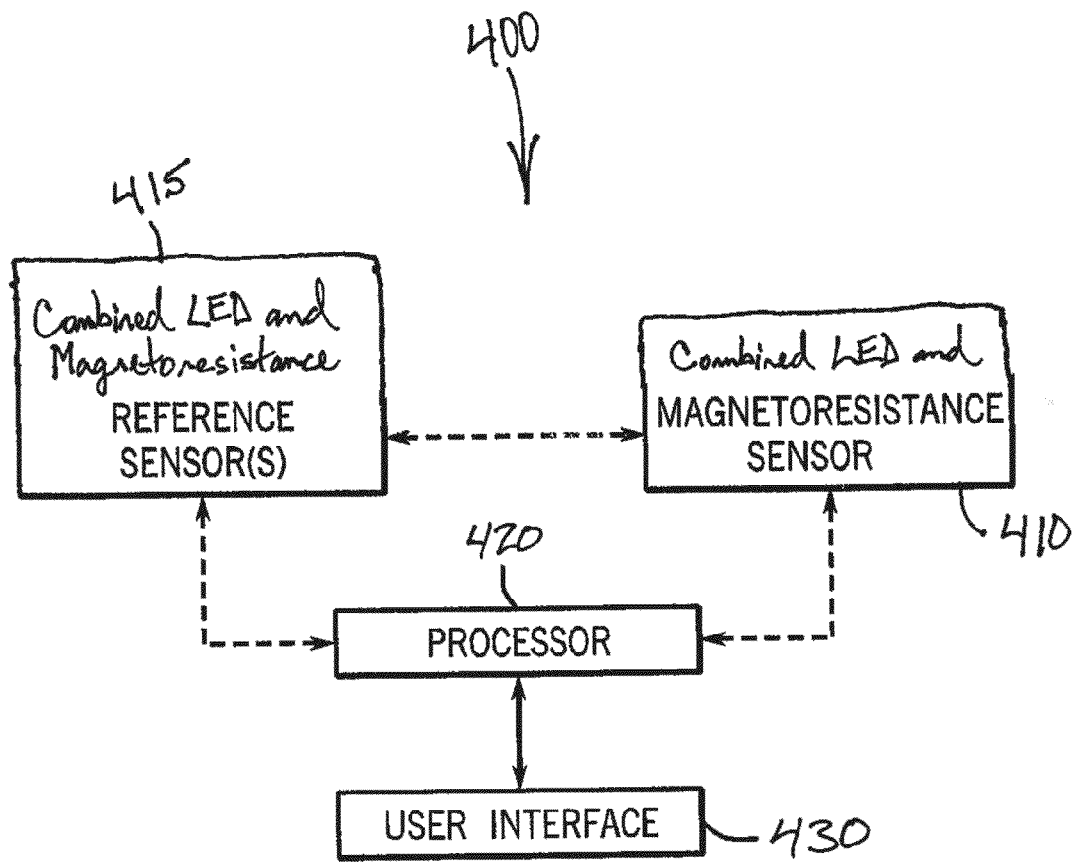
FIG. 4 is a block diagram of an exemplary embodiment of a hybrid tracking system.

FIG. 4 illustrates a block diagram of an exemplary embodiment of a hybrid tracking system 400. The hybrid tracking system 400 may be used for medical applications such as image-guided surgery or interventional procedures. The hybrid tracking system 400 includes at least three (3) combined LED and magnetoresistance sensors 410 and at least one combined LED and magnetoresistance reference sensor 415. The at least three (3) combined LED and magnetoresistance sensors 410 and at least one combined LED and magnetoresistance reference sensor 415 are coupled to at least one processor 420. In turn, the at least one processor 420 is coupled to a user interface 430. The user interface 430 may include a display for displaying position and orientation information to an operator.

The combined LED and magnetoresistance sensors 410 may be attached to objects to be tracked. The combined LED and magnetoresistance reference sensor 415 may be attached to a fixed object. For example, the combined LED and magnetoresistance reference sensor 415 may be attached to an anatomical reference of a patient undergoing a medical procedure, an imaging system, a table or other fixed structure.

The combined LED and magnetoresistance reference sensor 415 may communicate with and receive signals from the combined LED and magnetoresistance sensors 410. The at least one processor 420 is coupled to and receives signals from the combined LED and magnetoresistance reference sensor 415 and the combined LED and magnetoresistance sensors 410. According to various exemplary embodiments, the signals may be transmitted from the combined LED and magnetoresistance sensors 410 and the combined LED and magnetoresistance reference sensor 415 to the processor 420 using either wired or wireless communication protocols and interfaces. The hybrid tracking system 400 provides the ability to track and display the position and orientation of multiple objects having combined LED and magnetoresistance sensors 410 attached thereto.

The combined LED and magnetoresistance sensors 410 and the combined LED and magnetoresistance reference sensor 415 may generate optical and EM signals. These signals may be available simultaneously. The signals from the combined LED and magnetoresistance sensors 410 along with the combined LED and magnetoresistance reference sensor 415 are provided to the processor 420. The processor 420 is configured to select a signal from the combined LED and magnetoresistance sensors 410 or the combined LED and magnetoresistance reference sensor 415 using either the optical tracking technology or the EM tracking technology. For example, for the optical tracking technology to work, a line of sight path is required. If the line of sight path is not available, the processing unit 420 may select a signal from magnetoresistance sensor. Likewise if a signal from the magnetoresistance sensor is distorted due to the presence of a nearby metal distorter or other EM noise in the environment, the processing unit 420 may select a signal from the LED. By including at least three (3) combined LED and magnetoresistance sensors 410 in the hybrid tracking system 400, the hybrid tracking system may be used to track at least one object using either the optical tracking technology or the EM tracking technology. In addition, the combined LED and magnetoresistance reference sensor 415 may be used as a dynamic reference for either the optical tracking technology or the EM tracking technology.

The processor 420 is illustrated conceptually and may be implemented using any combination of dedicated hardware boards, digital signal processors, field programmable gate arrays, and processors. For example, the processor may include memory, which may be either volatile or non-volatile media. In addition, the processor may also include either removable or non-removable storage media. Alternatively, the processor may be implemented using an off-the-shelf computer with a single processor or multiple processors, with the functional operations distributed between processors.

An exemplary system for implementing the processor 420 and/or user interface 430 may include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

Figure 5:
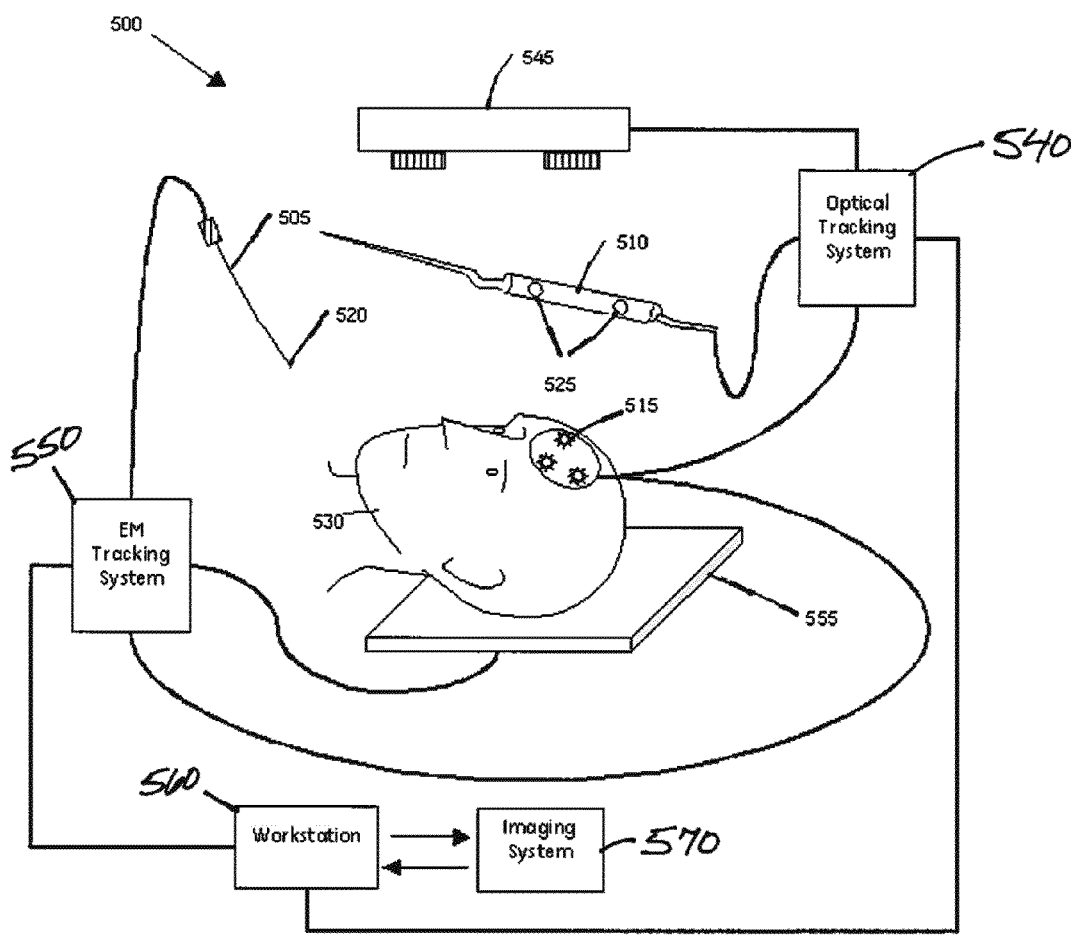
FIG. 5 is a schematic diagram of an exemplary embodiment of a hybrid tracking system.

FIG. 5 illustrates a schematic diagram of an exemplary embodiment of a hybrid tracking system 500. In an exemplary embodiment, the hybrid tracking system 500 implements both EM and optical tracking technologies. The hybrid tracking system 500 includes at least one combined LED and magnetoresistance sensor 515 to determine the position and orientation of at least one object, instrument, implant or other medical device being tracked. The at least one combined LED and magnetoresistance sensor 515 may be attached to at least one object, instrument, implant or other medical device being tracked or to a patient 530 to act as a dynamic reference sensor. The hybrid tracking system 500 is configured such that the at least one object, instrument, implant or other medical device may be tracked using either optical tracking technology or EM tracking technology. For example as shown in FIG. 5, an instrument 505 may be magnetically tracked using magnetoresistance sensor 520, and an instrument 510 may be optically tracked using LEDs 525. Alternatively, the instruments 505 and 510 may be tracked with either optical or EM tracking technologies using combined LED and magnetoresistance sensors.

The hybrid tracking system 500 includes an optical tracking system 540 to detect the light produced by LEDs from the at least one combined LED and magnetoresistance sensor 515 and/or LEDs 525 coupled to an optically tracked instrument 510. LEDs 525 emits light, reflecting movement of instrument 510, which is capable of being optically tracked. At least one optical sensor such as camera system 545 is provided for light detection from LEDs in the at least one combined LED and magnetoresistance sensor 515 and LEDs 525 coupled to the optically tracked instrument 510. The camera system 545 may include multiple cameras coupled to the optical tracking system 540 and coupled to a workstation 560, which may be coupled to an imaging system 570. The optical tracking system 540 works with either active LEDs that are visible to the camera system 545 or with passive spherical reflectors that reflects light generated by a light source such as an infra-red light source and detected by camera system 545. Generally, at least three (3) LEDs may be seen by at least two (2) cameras in the camera system 545 and are provided to determine the position of the LEDs in space. At least two (2) LEDs may be used for simple instruments, such as a pointer. By knowing the fixed mechanical positions of the LEDs and comparing the measured locations of the LEDs, the position and orientation of an object with LEDs attached thereto may be determined and tracked. Alternatively, magnetoresistance sensor information may be used to determine the relative position of the LEDs on an object being tracked with the optical tracking system 540.

The hybrid tracking system 500 also includes an EM tracking system 550 to detect and process the output of the magnetoresistance sensor 520 and the at least one combined LED and magnetoresistance sensor 515. The hybrid tracking system 500 may further include an EM transmitter 555, which is a magnetic field generator. The magnetoresistance sensor in the combined LED and magnetoresistance sensor 515 provides an output corresponding to a change in electrical resistance of a conductor or semiconductor when a magnetic field is applied to the sensor. The magnetoresistance sensor provides a signal in response to the strength and direction of the magnetic field. The EM tracking system 550, EM transmitter 555, and the magnetoresistance sensor or the magnetoresistance sensor in the combined LED and magnetoresistance sensor 515 work together to track a magnetically trackable instrument 505.

The workstation 560 is provided to process the signals from the optical tracking system 540 and the EM tracking system 550. The workstation 560 may include memory, a display, and a control unit. For example, the workstation 560 may include a general-purpose computer or processor with memory, or a separate processor and/or memory, and the display could include a visual monitor. The workstation 560 may also include a user interface (which may include, for example, a mouse, keyboard, touch screen, or other input device).

The workstation 560 is also configured to work with the imaging system 570 by controlling operation of the imaging system 570 and processing images acquired by the imaging system 570. The imaging system 570 may be used to generate radiological images of a patient's anatomy to aid in planning and/or performing medical, surgical or interventional procedures. The images of the patient's anatomy may be generated either prior to or during the medical, surgical or interventional procedure. For example, any suitable medical imaging system may be used, such as X-ray, computed tomography (CT), magnetic resonance (MR), positron emission tomography (PET), ultrasound, or any other suitable imaging technology, as well as any combinations thereof. In an exemplary embodiment, the imaging system 570 is a fluoroscopic imaging system.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A combined LED and magnetoresistance sensor comprising:
   at least one magnetoresistance sensor; and
   at least one light emitting diode (LED);
   wherein the magnetoresistance sensor and the LED are integrated into a single package; and
   wherein the at least one magnetoresistance sensor comprises:
      an insulating substrate;
      an alternating pattern of a metal material and a semiconductor material deposited on a surface of the insulating substrate; and
      a bias magnet material deposited over the alternating pattern of a metal material and a semiconductor material.

2. The combined LED and magnetoresistance sensor of claim 1, wherein the at least one magnetoresistance sensor and the at least one LED are fabricated as separate semiconductor integrated circuits and are bonded together.

3. The combined LED and magnetoresistance sensor of claim 1, wherein a non-active layer of the at least one magnetoresistance sensor and a non-active layer of the at least one LED are bonded together with an epoxy.

4. The combined LED and magnetoresistance sensor of claim 1, wherein the at least one magnetoresistance sensor and the at least one LED are fabricated as a single semiconductor integrated circuit.

5. The combined LED and magnetoresistance sensor of claim 1, wherein the bias magnet material subjects the semiconductor material to a magnetic field.

6. The combined LED and magnetoresistance sensor of claim 5, wherein the at least one magnetoresistance sensor provides a signal in response to a strength and a direction of the magnetic field.

7. The combined LED and magnetoresistance sensor of claim 5, wherein the magnetic field increases the resistance of the at least one magnetoresistance sensor.

8. The combined LED and magnetoresistance sensor of claim 1, wherein the at least one LED comprises:
   a substrate;
   a p-doped region;
   an n-doped region; and
   an activation layer deposited between the p-doped region and the n-doped region;
   wherein either the p-doped region or the n-doped region is adjacent to the substrate.

9. The combined LED and magnetoresistance sensor of claim 1, wherein the at least one magnetoresistance sensor is configured to provide a signal in response to an applied magnetic field and the at least one LED is configured to emit a signal in response to an applied voltage.

10. The combined LED and magnetoresistance sensor of claim 1, wherein the at least one magnetoresistance sensor and the at least one LED are mounted within a reflector cup.

11. The combined LED and magnetoresistance sensor of claim 1, wherein the at least one magnetoresistance sensor and the at least one LED are encapsulated within an encapsulating lens.

12. The combined LED and magnetoresistance sensor of claim 1, further comprising at least two leads extending from the at least one magnetoresistance sensor and the at least one LED.

13. A hybrid tracking system comprising:
   at least one combined LED and magnetoresistance reference sensor attached to a fixed object for generating an electromagnetic field and creating a tracking volume in a surgical field;
   at least one combined LED and magnetoresistance sensor associated with an object being tracked in the tracking volume within the surgical field; and
   at least one processor coupled to the at least one combined LED and magnetoresistance reference sensor and the at least one combined LED and magnetoresistance sensor, wherein the at least one processor is capable of processing signals from the at least one combined LED and magnetoresistance reference sensor and the at least one combined LED and magnetoresistance sensor.

14. The hybrid tracking system of claim 13, further comprising at least one optical tracking technology device and at least one electromagnetic (EM) tracking technology device.

15. The hybrid tracking system of claim 13, wherein the at least one combined LED and magnetoresistance reference sensor includes at least one LED and at least one magnetoresistance sensor integrated into a single package.

16. The hybrid tracking system of claim 13, wherein the at least one combined LED and magnetoresistance sensor includes at least one LED and at least one magnetoresistance sensor integrated into a single package.

17. A hybrid tracking system utilizing at least one combined LED and magnetoresistance sensor, the hybrid tracking system comprising:
   at least one combined LED and magnetoresistance reference sensor attached to a fixed object for generating an electromagnetic field and creating a tracking volume in a surgical field;
   at least one combined LED and magnetoresistance sensor attached to an object being tracked in the tracking volume within the surgical field;
   at least one optical tracking technology device including a camera system to sense light emitted by a LED;

at least one EM tracking technology device including an EM transmitter for generating an electromagnetic field; and at least one processor coupled to the at least one combined LED and magnetoresistance reference sensor and the at least one combined LED and magnetoresistance sensor, wherein the at least one processor is capable of processing signals from the at least one combined LED and magnetoresistance reference sensor and the at least one combined LED and magnetoresistance sensor.

18. The hybrid tracking system of claim 17, wherein the at least one combined LED and magnetoresistance reference sensor includes at least one LED and at least one magnetoresistance sensor integrated into a single package.

19. The hybrid tracking system of claim 17, wherein the at least one combined LED and magnetoresistance sensor includes at least one LED and at least one magnetoresistance sensor integrated into a single package.

* * * * *